United States Patent [19]

Strand et al.

[11] Patent Number: 5,407,368

[45] Date of Patent: Apr. 18, 1995

[54] ELECTRODE CONNECTOR

[75] Inventors: Jerome E. Strand, Hudson, Wis.; Perry S. Dotterman, Maplewood, Minn.

[73] Assignee: Minnesota Mining and Manufacturing Company, St. Paul, Minn.

[21] Appl. No.: 990,692

[22] Filed: Dec. 15, 1992

[51] Int. Cl.⁶ .............................................. H01R 4/48
[52] U.S. Cl. ....................................... 439/729; 439/909
[58] Field of Search ................... 439/86, 87, 90, 729, 439/819, 822, 909; 128/639, 640, 783, 798

[56] References Cited

U.S. PATENT DOCUMENTS

| | | |
|---|---|---|
| Re. 24,906 | 12/1960 | Ulrich . |
| Re. 31,454 | 12/1983 | Hymes .............................. 128/641 |
| Re. 33,353 | 9/1990 | Heinecke .......................... 428/40 |
| D. 244,879 | 6/1977 | Manno . |
| D. 328,283 | 6/1977 | Strand . |
| 3,090,029 | 5/1963 | Stroebel . |
| 3,389,827 | 5/1968 | Abere et al. . |
| 3,641,473 | 2/1972 | Attaway ....................... 439/729 X |
| 3,644,877 | 2/1972 | Carbonneau . |
| 3,976,055 | 8/1976 | Monter et al. ............... 128/2.06 E |
| 4,061,408 | 12/1977 | Bast et al. . |
| 4,112,213 | 9/1978 | Waldman ........................ 526/279 |
| 4,166,465 | 9/1979 | Esty et al. ...................... 128/303 |
| 4,178,052 | 12/1979 | Ekbom et al. . |
| 4,310,509 | 1/1982 | Berglund et al. . |
| 4,323,557 | 4/1982 | Rosso et al. ..................... 424/28 |
| 4,391,278 | 7/1983 | Cahalan et al. ................. 128/640 |
| 4,539,996 | 9/1985 | Engel ............................. 128/640 |
| 4,543,958 | 10/1985 | Cartmell ......................... 128/640 |
| 4,554,924 | 11/1985 | Engel ............................. 128/640 |
| 4,555,155 | 11/1985 | Drake . |
| 4,640,563 | 2/1987 | LeBlanc . |
| 4,657,023 | 4/1987 | Kuhn .............................. 128/640 |
| 4,679,563 | 7/1987 | Wada et al. ..................... 128/640 |
| 4,694,835 | 8/1987 | Strand ............................. 128/640 |
| 4,700,997 | 10/1987 | Strand ............................. 439/372 |
| 4,702,256 | 10/1987 | Robinson et al. ............... 128/639 |
| 4,732,808 | 3/1988 | Krampe et al. ................. 428/355 |
| 4,795,516 | 1/1989 | Strand ............................. 156/235 |
| 4,797,125 | 1/1989 | Malana ........................... 439/729 |
| 4,798,208 | 1/1989 | Faasse, Jr. ...................... 128/160 |
| 4,798,642 | 1/1989 | Craighead et al. ............. 156/252 |
| 4,842,558 | 6/1989 | Strand ............................. 439/863 |
| 4,848,353 | 8/1989 | Engel .............................. 128/640 |
| 4,852,571 | 8/1989 | Gadsby et al. .................. 128/640 |
| 4,915,656 | 4/1990 | Alferness ........................ 439/729 |
| 4,917,928 | 4/1990 | Heinecke ........................ 428/41 |
| 4,917,929 | 4/1990 | Heinecke ........................ 428/41 |
| 4,922,911 | 5/1990 | Wada et al. ..................... 128/640 |
| 4,952,177 | 8/1990 | Drake et al. .................... 439/828 |
| 5,012,810 | 5/1991 | Strand et al. ................... 128/640 |
| 5,058,589 | 10/1991 | Ding et al. ..................... 128/640 |
| 5,078,138 | 1/1992 | Strand et al. ................... 128/640 |
| 5,078,139 | 1/1992 | Strand et al. ................... 128/640 |
| 5,133,355 | 7/1992 | Strand et al. ................... 128/640 |
| 5,178,144 | 1/1993 | Cartmell ......................... 128/640 |
| 5,195,523 | 3/1993 | Cartmell et al. ............. 439/86 X |
| 5,209,679 | 5/1993 | Quinlan . |
| 5,295,872 | 3/1994 | Christensson . |

FOREIGN PATENT DOCUMENTS

| | | |
|---|---|---|
| 0051935A2 | 5/1982 | European Pat. Off. . |
| 0210020 | 1/1987 | European Pat. Off. . |
| 0510786A1 | 10/1992 | European Pat. Off. . |
| 3307896 | 9/1984 | Germany . |
| 0648067 | 12/1950 | United Kingdom ............. 439/729 |
| 1519782 | 8/1978 | United Kingdom . |

OTHER PUBLICATIONS

"Human Factors Design Handbook" Information and Guidelines for the Design of Systems, Facilities, Equipment, and Products for Human Use by Wesley E. Woodson, President, Man Factors, Inc., McGraw-Hill Book Company, pp. 611 and 774.
"Human Factors Design Handbook," by Wesley E. Woodson (3 pages).
"Melinex Technical Data", ICI Americas Inc., Form No. 5773h(C), dated Dec. 1986 (5 pages).

Primary Examiner—Khiem Nguyen
Attorney, Agent, or Firm—Gary L. Griswold; Walter N. Kirn; Jeffrey J. Hohenshell

[57] ABSTRACT

A connector for use with a tab style biomedical electrode is disclosed. The connector comprises pivotally mounted movable and fixed jaws and a spring biasing the jaws toward a closed position. The connector provides a high tab release force and yet provides an acceptably low actuation force. Preferably, the fixed jaw includes a smooth, continuous surface which facilitates insertion of the tab between the jaws of the connector.

50 Claims, 6 Drawing Sheets

ELECTRODE CONNECTOR

THE FIELD OF INVENTION

The present invention relates to connectors for biomedical electrodes having an electrically conductive contacting tab with generally flat upper and lower surfaces.

BACKGROUND

The art is replete with different types of biomedical electrodes which have an electrically conductive contacting tab. Examples of such biomedical electrodes are described in U.S. Pat. Nos. 4,543,958 to Cartmel, 4,798,208 to Faasse, Jr., 5,012,810 to Strand et al., 5,078,138 to Strand et al., 5,078,139 to Strand et al., 5,133,356 to Bryan et al., and U.S. patent application Ser. No. 07/686,049, the entire contents of each of which are herein expressly incorporated by reference. Particular examples of such electrodes include 3M Red Dot TM ECG and EKG electrodes generally available from the Minnesota Mining and Manufacturing Co. (3M) of St. Paul, Minn. Typically, such electrodes have a substantially flat construction which leads to significant advantages including: (1) such an electrode is less conspicuous when worn under a patient's clothes and less obstructive to other medical procedures, and (2) the low profile of tab-style electrodes provides a structure which is free of any substantial projections that might cause discomfort for a patient should the patient be bumped in the vicinity of the electrode or should the patient lie down on the electrode.

The art is also replete with connectors for electrically connecting medical equipment to a tab-style electrode. For example such medical equipment may comprise electrical receiving instrumentation, diagnostic equipment, stress monitoring equipment or other testing equipment for detecting a patient's electrical signals. Other examples of medical equipment include therapeutic electrical instrumentation such as transcutaneous electronic nerve stimulation (TENS) devices used for pain management and neuromuscular stimulation (NMS) equipment used for treating conditions such as scoliosis. Such medical equipment may also include the equipment used in electrosurgery or equipment used with defibrillation pads for emergency cardiac treatment.

Examples of connectors for connecting medical equipment to a tab-style biomedical electrode include U.S. Pat. Nos. 4,061,408 to Bast et al., 4,555,155 to Drake, 4,700,997 to Strand, 4,842,558 to Strand, and 4,952,177 to Drake et al.

The art also includes "alligator" type electrical connectors. An "alligator" type electrical connector typically includes a fixed jaw and a movable jaw, a pin for mounting the movable jaw for pivotal movement relative to the fixed jaw between tab accept and closed positions and a spring for biasing the movable jaw toward the closed position. A leadwire is typically fixedly connected to the fixed jaw so that the fixed jaw does not move relative to the leadwire. As used herein, the term "fixed jaw" when used to describe one of the jaws of an "alligator" type connector, means that jaw which remains stationary or fixed relative to the leadwire when the connector is opened. Particular examples of "alligator" type electrical connectors include U.S. Pat. Nos. 3,090,029 to Stroebel, 3,644,877 to Carbonneau, 4,797,125 to Malana, 4,702,256 to Robinson et al., and 5,058,589 to Ding et al.

Prior art "alligator" type electrical connectors suffer from many drawbacks. In order to ensure a very high pull off force of the connector from the tab, some prior art "alligator" type electrical connectors include a very strong spring which renders the electrical connector difficult to open. Also, some prior art electrical connectors include a hole, depression, groove, slot, slit or other discontinuous surface in a jaw which is designed to deflect the tab of the electrode. Such deflection of the tab generally results in a higher grasping force for the tab but also tends to mar, puncture or otherwise damage the conductive surface of the electrically conductive contacting tab of the biomedical electrode. Such damage may potentially result in a loss of continuity or may otherwise adversely affect the electrical properties of the biomedical electrode.

Some jaws of prior art "alligator" electrical connectors include teeth, abutment surfaces, labyrinth-like or tortuous paths or an otherwise rough surface. A rough surface may include a structure that substantially deforms or deflects the electrode contacting tab during insertion of the tab into the connector. Again, the deflection of the tab into a surface irregularity may increase the tab pull off force of the connector, but not without costs. The rough surface may "catch" the electrically contacting tab and cause the contacting tab to bend or otherwise deform while the tab is being inserted into the connector. Such action may render the electrical connector difficult to place on the tab of an electrode.

Also, the V-shaped nature of many prior art "alligator" type connectors render them particularly susceptible to tangling with the leadwires of other leadwires and connectors as the leadwire of one assembly may easily slip between proximal ends of the fixed and movable jaws of another assembly.

Finally, some existing prior art "alligator" type electrical connectors may be unsuitable for biomedical use as they have relatively sharp portions which may be uncomfortable for some patients. For example, should the patient roll on top of the connector, a sharp edge or tooth may cause discomfort for the patient.

BRIEF DESCRIPTION OF THE INVENTION

The present invention provides a connector for a biomedical electrode having a generally flat, electrically conductive contacting tab. The connector comprises a fixed jaw having a tab engagement surface, a movable jaw having a tab engagement surface and a manually engagable actuation surface, a pivotable mounting mechanism for mounting the movable jaw for pivotable movement relative to the fixed jaw between the tab accept position and a close position, and a spring for biasing the movable jaw toward the closed position.

Preferably the fixed jaw comprises smooth, continuous tab engagement and lead-in surfaces, and the movable jaw comprises a tooth portion having a tab engagement surface, and a smooth lead-in surface. The tooth portion preferably comprises two teeth having a groove therebetween.

The present invention provides a connector which: 1) provides an actuation force less than about nine (9) pounds so that a broad range of user's may open the jaws of the connector while maintaining a desirable tab retention force, 2) preferably provides smooth tab engagement surfaces on one jaw which restrict damage to the tab of the electrode and which facilitate insertion of the tab between the jaws of the connector, 3) preferably provides a jaw with a continuous tab engagement surface to restrict excessive deflection of the tab of the electrode when it is clamped between the jaws of the connector to thereby restrict damage to the tab of the electrode, 4) may be constructed from X-Ray translucent materials, 5) is particularly suitable for use with a tab-style electrode comprising a tab with a stiff-flexible layer and a flexible-deformable second layer, 6) restricts the likelihood that the connector and its leadwire may become entangled with another connector/leadwire assembly or itself, 7) presents a low-profile which results in numerous advantages including comfort for the patient, 8) includes grasping or "manually activation" surfaces which conform to the shape of a user's digits, and 9) is free of sharp surfaces that might cause discomfort for a patient should the patient be bumped in the vicinity of the connector or should the patient lie down on the connector.

BRIEF DESCRIPTION OF THE DRAWING

The present invention will be further described with reference to the accompanying drawing wherein like reference numerals refer to like parts in the several views, and wherein.

DETAILED DESCRIPTION

FIGS. 2 through 6 of the drawing show a first embodiment of connector according to the present invention generally designated by the reference character 10. The connector 10 is adapted for use with a biomedical electrode having an electrically conductive contacting tab.

Examples of suitable biomedical electrodes are found in U.S. Pat. Nos. 4,543,958 to Cartmel, 4,798,208 to Faasse, Jr., 5,012,810 to Strand et al., 5,078,138 to Strand et al., 5,078,139 to Strand et al., 5,133,355 to Strand et at.; 5,133,356 to Bryan et al., and U.S. patent application Ser. No. 07/686,049, the entire contents of which are herein expressly incorporated by reference. The connector 10 may be used with biomedical electrodes having widely varying thicknesses of electrically conductive tabs.

The connector 10 is particularly suitable for use with a biomedical electrode 14 having a firm, but flexible layer and a deformable layer. In particular, the biomedical electrode may comprise the electrode described in U.S. Pat. No. 5,133,356 to Bryan et al. the entire contents of which are herein expressly incorporated by reference.

Figure 1:
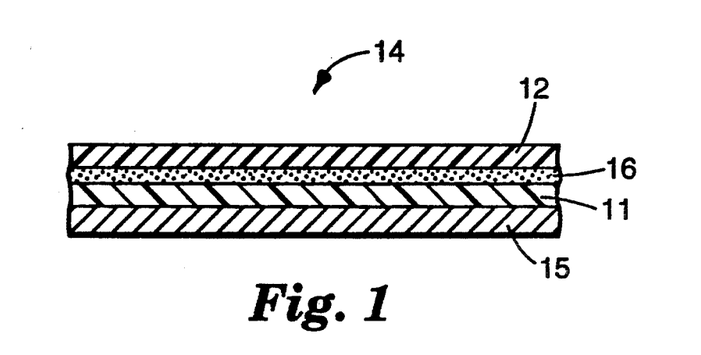
FIG. 1 is an exaggerated schematic view of portions of the electrically conductive tab of one example of biomedical electrode for use with the connector of the present invention.

FIG. 1 is a schematic illustration of a portion of the electrically conductive contacting tab of a biomedical electrode 14 having a firm, but flexible layer 11 and a deformable layer 12. The material used to construct the firm, flexible layer 11 preferably is constructed from a material that resists substantial permanent plastic deformation under forces exerted by the jaws of a connector, and is compatible with known processes for vapor coating silver. Such processes are used to coat a silver/silver chloride conductive coating 15 onto the layer 11.

Suitable materials for the layer 11 include, but are not limited to Scotchpar brand 3 mil PET film, commercially available from the Minnesota Mining and Manufacturing Co. (3M) of St. Paul, Minn., a polyester film commercially available as "Melinex" 505-300, 329 or 339 film from ICI Americas of Hopewell, Va. (coated with a silver/silver chloride ink commercially available as "R-300" ink from Ercon, Inc. of Waltham, Mass.), or a web of polyester/cellulose fibers commercially available as "Manniweb" web from Lydall, Inc. of Troy, N.Y. (having a carbon ink commercially available as "SS24636" ink from Acheson Colloids Company of Port Huron, Mich.).

Preferably, the material used to construct layer 11 is a 3 mil (0.075 mm) thick strip of polyethylene terephthalate film. The properties of the film included a tensile strength of about 28,000 psi in a machine direction, approximately 35,000 psi in the transverse direction, both as measured according to ASTM D882A. The coefficient of dynamic friction of this film is about 0.5 as measured by ASTM D1894. The commercial source of this film is ICI Films of Wilmington, Del., branded as "Melinex" 505.

The deformable layer 12 should be substantially softer than the layer 11 so that the layer 12 deforms in response to being clamped by the jaws of the connector 10. The deformable layer 12 enhances mechanical contact between the connector 10 and the electrode 14.

The layer 12 is adhered to the layer 11 by a layer of adhesive 16 such as a conventional acrylate adhesive. The adhesive may comprise a layer of 95.5%/4.5% isooctyl acrylate/acrylic acid copolymer adhesive, coated to a weight of 920 mg/200 cm² of backing area. However, any suitable adhesive may be utilized so long as the adhesive resists shear between the layers 11 and 12 and is compatible with the materials used to construct the layers 11 and 12.

Suitable materials for the layer 12 include, but are not limited to, a low density polyethylene such as NA 964-226, commercially available from Quantum Chemical of Rolling Meadows, Ill. This material may be extruded into a film with a thickness between about 0.002 to about 0.007 inches (0.005 to 0.013 cm), and preferably has a hardness of about 48 on the Shore D scale when measured according to ASTM Standard D2240, and in selecting alternative materials, those having a hardness between about 45 to 55 Shore D are believed to be particularly suitable. The commercial source of the layer 12 and adhesive 16 tape is Minnesota Mining and Manufacturing (3M) Company, of St. Paul, Minn., branded as "Blenderm" tape.

Referring now to FIGS. 2 through 6 of the drawings, there is shown the connector 10. The connector 10 comprises fixed 20 and movable 21 jaws, and a pivotal mounting means for mounting the movable jaw 21 for pivotal movement relative to the fixed jaw 20 between a tab accept position with the fixed jaw 20 spaced from the movable jaw 21 so that the tab of the biomedical electrode (e.g. 14) may be received between 9 the jaws 20 and 21, and a closed position (FIG. 3) with fixed 20 and movable 21 jaws spaced more closely than in the tab accept position.

The movable jaw 21 comprises proximal and distal ends, a top surface 24 and a bottom surface 25. The fixed jaw 20 comprises a bottom surface 27, proximal and distal end portions terminating in proximal and distal ends with the proximal end portion having a top surface 26. At the proximal end of the fixed jaw 20, the connector is adapted to be connected to a leadwire L having an outside diameter.

The connector 10 is elongate and has a longitudinal axis along its length (preferably about 1.5 inches). The connector 10 has an overall height (preferably about 0.38 inches, but should be less than about 1.5 inches and more preferably less than about 0.5 inches) presenting a low profile connector and an overall width (preferably about 0.54 inches). The overall width is preferably at least 1.1 times greater than the overall height of the connector. Providing a connector with an overall width that is greater than its height is believed to provide a connector with resists rolling about its longitudinal axis.

The connector 10 may optionally include various features which conform the connector's operative surfaces to the general shape of a user's hand. For example, the bottom surface 27 of the fixed jaw 20 comprises an arcuate portion for conforming to the shape of a user's digits. For example the arcuate portion may be arcuate about an axis that is perpendicular to the longitudinal axis of the connector 10 and may have a radius of curvature of about 1.25 inches. The vertical distance from the top of surface 27 in FIG. 3 to its bottom is preferably about 0.06 inches.

The manually engagable actuation surface 32 may optionally include a locating means for assisting users in placing their digits in the desired position on the movable jaw 21. The locating means may comprise a rib, detent, depression, groove or slot in the desired position on the top surface 24 of the movable jaw 21.

The pivotal mounting means comprises a recess portion 18 recessed from the top surface 26 of the fixed jaw 20, and a pin 19 situated between the proximal and distal ends of the movable jaw 21 so that the movable jaw 21 can pivot about the axis of the pin 19. Preferably, the pin 19 may be integrally molded with the movable jaw 21 so that the pin and movable jaw form one, monolithic piece. Alternatively, the pin may comprise a metal pin adapted to be received in a slot in the movable jaw and fixed jaw.

Figure 4:
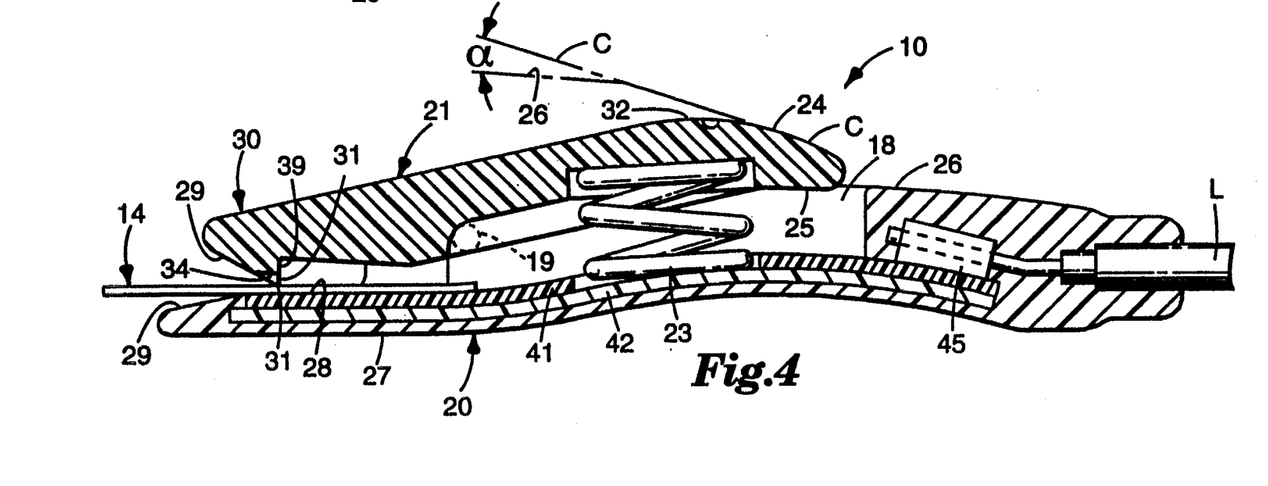
FIG. 4 is a reduced sectional view similar to FIG. 3 except that FIG. 4 illustrates an electrically conductive tab of a biomedical electrode clamped between the fixed and movable jaws.
Figure 5:
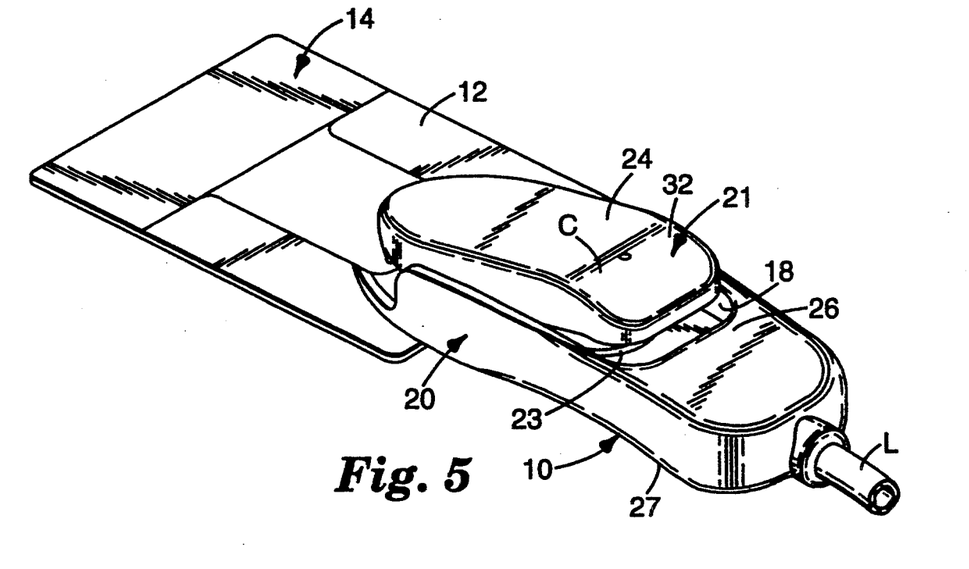
FIG. 5 is a perspective view of the connector of FIG. 2 illustrating an electrically conductive tab of a biomedical electrode clamped between the fixed and movable jaws.

The pin 19 is adapted to be received in a pivot groove in the fixed jaw 20 so that the movable jaw 21 can pivot about the axis of the pin 19 when a user manually presses on actuation surface 32. As best seen in FIG. 4, the pin 19 is situated to allow the tab of the electrode to be situated directly between the pin 19 and the fixed jaw 20. When it is said that the tab of the electrode is situated "directly between" the pin 19 and the fixed jaw 20, it is meant that, in FIG. 4, if a line is drawn vertically through the pin 19 and jaw 20, it would intersect a portion of the electrode's tab. This feature of the present invention affords the use of the connector 10 for a variety of sizes of tabs and also affords full insertion of the tab into the connector.

In the closed position (FIG. 3), the distance D between the top surface 26 of the fixed jaw 20 and the bottom surface 25 of the movable jaw 21 at the proximal end of the movable jaw 21 is less than the outside diameter of the leadwire L. For example, the distance D may be approximately 0.06 inches. This feature of the present invention restricts the chances that a leadwire L will become caught between the movable and fixed jaws of a connector, thereby restricting the chances that the connector 10 will become entangled with a leadwire L.

Figure 3:
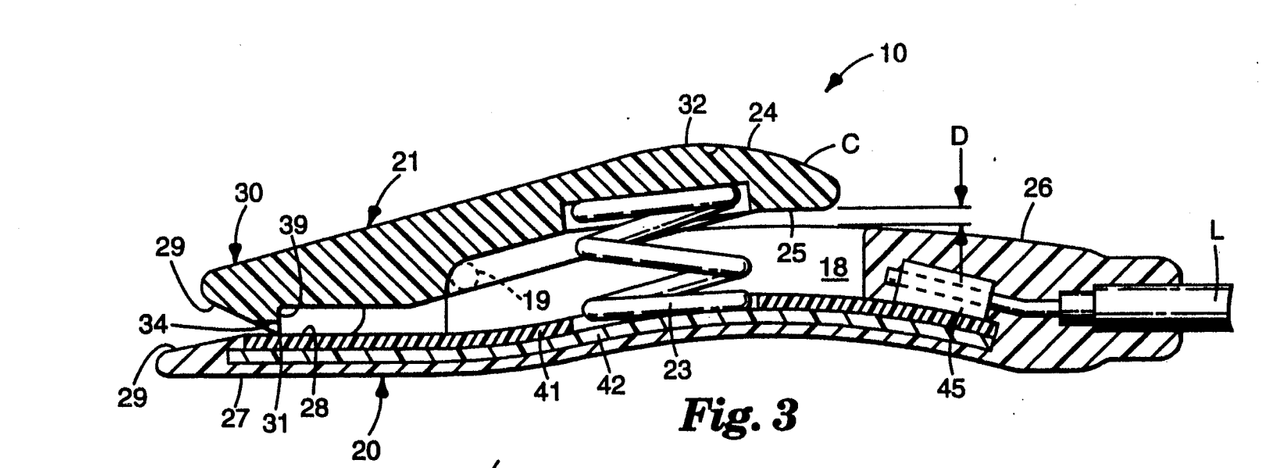
FIG. 3 is a reduced sectional view of the connector of FIG. 2 taken approximately along lines 3—3 of FIG. 2, but which illustrates an unsectioned spring, and which illustrates a fixed and movable jaw in a closed position.

Another feature of the present invention that restricts the chances that the connector 10 will become entangled with a leadwire L is that the movable jaw 21 comprises a cam surface C generally adjacent its proximal end (See FIGS. 3 and 4). As shown in FIG. 3, the cam surface C is situated at an acute angle (alpha) relative to the top surface 26 of the fixed jaw 20. Thus, it is believed that when a leadwire L comes into contact with the cam surface C, the cam surface C will tend to move the leadwire L away from the recess portion 18 and away from becoming caught between the movable jaw 21 and fixed jaw 20.

The connector 10 also includes a biasing means such as a coil spring 23 for biasing the movable jaw 21 toward the closed position. While the biasing means is shown as a coil spring, it should be noted that the biasing means may comprise any suitable biasing means such as, but not limited to a leaf spring, a leaf spring integrally molded into the fixed jaw, an elastomeric structure (e.g. an egg shaped elastomer between the fixed and movable jaws), or a torsion spring so long as the movable jaw is biased toward the closed position. The coil spring may be constructed from any suitable material such as a plastic or metal. Optionally, the coil spring may be constructed from a substantially X-ray translucent material such as, Hytrel 5556 or Hytrell 7246 polyester elastomers generally available from DuPont of Delaware.

As shown in FIGS. 3 and 4, preferably the fixed jaw 20 has a smooth, continuous tab engagement surface 28; and the movable jaw 29 has a tooth portion 30 with a tab engagement surface 31, and a manually engagable actuation surface 32. However, it should be noted that the position of the tooth portion and the smooth, continuous tab engagement surface may be reversed, that is, the movable jaw may have a smooth, continuous tab engagement surface and the fixed jaw may have the tooth portion.

Both the movable jaw 21 and the fixed jaw 20 have a smooth lead-in surface 29. Preferably, the lead-in surfaces 29 are continuous, generally planar surfaces and form an angle therebetween of about 40 degrees.

As used herein, when it is said that a surface is "smooth" surface (e.g. the tab engagement or lead-in surfaces), it is meant that the particularly referenced surface is free of any rough surfaces such as teeth, cylindrically shaped terminal portions, abutment surfaces, labyrinth-like or tortuous paths, or otherwise rough surface that may substantially deform, bend or deflect an electrode contacting tab during insertion of the tab into the jaws of the connector. A "smooth" tab engagement surface or lead-in surface is preferably a generally planar surface, but may comprise a slightly arcuate surface so long as the surface does not present a structure that is likely to bend, deform or otherwise deflect the electrode tab upon its insertion between the jaws of the connector.

As used herein, when it is said that a surface is a "continuous" surface (e.g. a tab engagement surface), it is meant that the particularly referenced tab engagement surface is free of any discontinuities such as a hole, depression, groove, slot, slit or other discontinuous surfaces which tend to substantially deflect the conductive tab of the electrode when it is clamped between the jaws of the connector. Such deflection may mar, puncture or otherwise damage the conductive surface of the electrically conductive contacting tab of the biomedical electrode that may potentially result in a loss of continuity or may otherwise adversely affect the electrical properties of the biomedical electrode. The discontinuity may also substantially deform, bend or deflect an electrode contacting tab during insertion of the tab into the jaws of the connector with the attendant disadvantages described above.

The fixed and movable jaws 20 and 21 comprise distal end portions having generally arcuate surfaces terminating in distal ends. The arcuate surfaces present blunt surfaces to a patient which reduces the chances that the connector will cause discomfort for the patient. The distal end of the movable jaw 21 is spaced proximally from the distal end of the fixed jaw 20.

Figure 2:
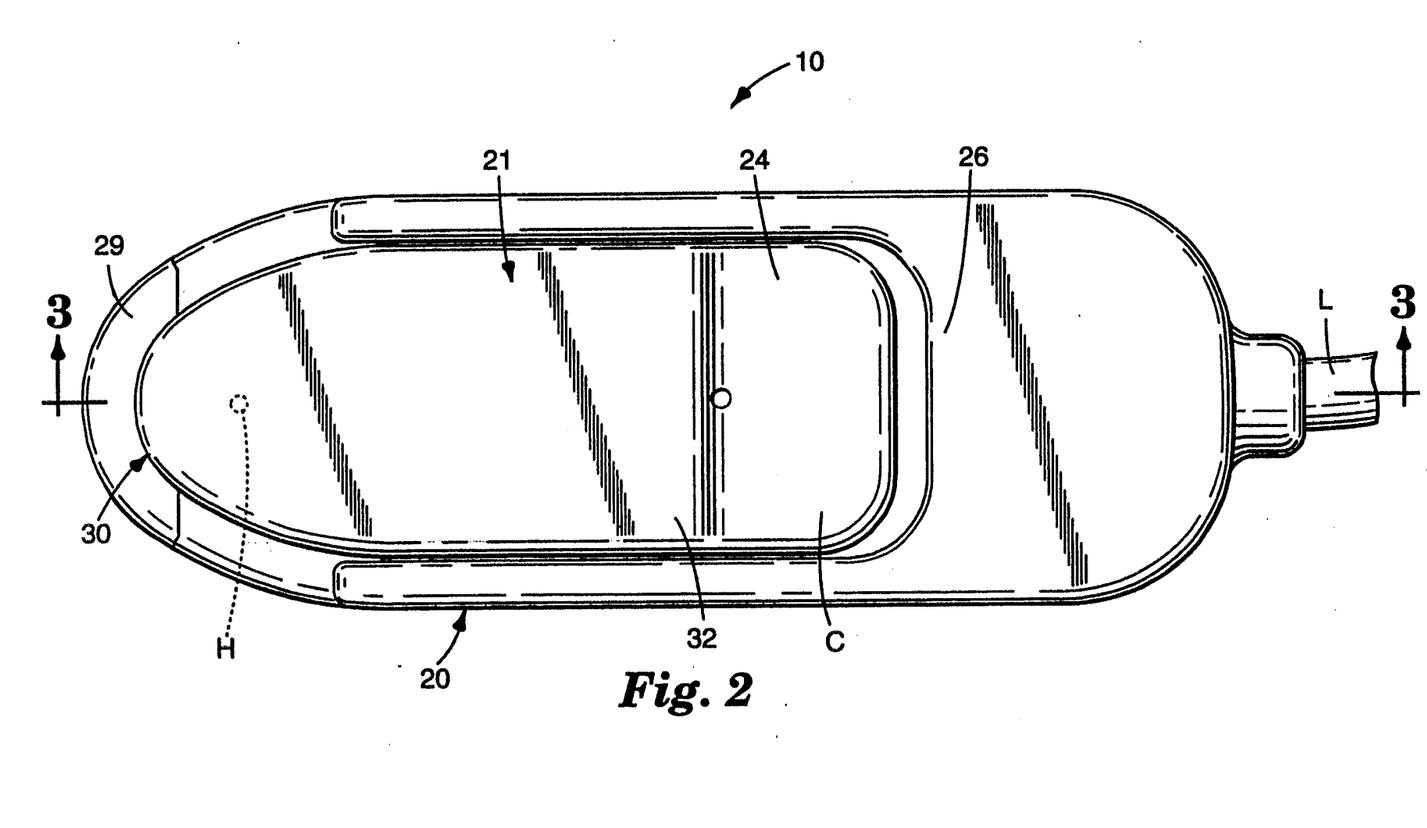
FIG. 2 is a top view of a first embodiment of connector according to the present invention illustrating a portion of a leadwire.

In addition to the smooth lead-in surfaces 29, the connector 10 also includes several features which further assist a user in placing the tab of the electrode between the fixed and movable jaws 20 and 21. For example, at each position along the longitudinal axis of the connector 10, the fixed jaw 20 is wider than the movable jaw 21. When the connector 10 is viewed from a top plane (as the connector is in FIG. 2), the distal end portion of the fixed jaw 20 encompasses the distal end portion of the movable jaw 21. In this view, a user can determine when a tab is placed between the movable and fixed jaws 20 and 21 as, when a tab is placed between the movable and fixed jaws, a portion of the fixed jaw 20 will no longer be seen as the tab will block a user's view. In this manner, the connector 10 is facilitates insertion of the tab between the jaws. Optionally, the movable jaw 21 may have a hole in its distal end portion for viewing the relative position of the tab of the electrode and the jaws of the connector. FIG. 2 also illustrates an optional hole H.

Figure 6:
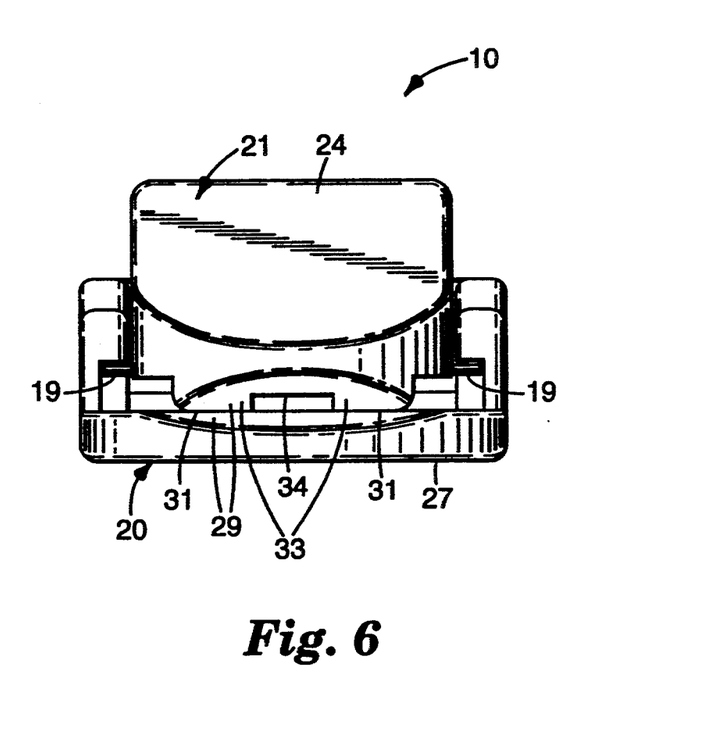
FIG. 6 is an enlarged front end view of the connector of FIG. 2 illustrating fixed and movable jaws in a closed position.

The tooth portion 30 preferably comprises a pair of teeth 33 as best seen in FIG. 6. The teeth 33 have a groove 34 therebetween, and each of the teeth 33 have a tab engagement surface 31. The groove 34 is believed to be particularly desirable when the connector 10 is used with a tab having a deformable layer 12 (e.g. a tab similar to the tab shown in FIG. 1). It is believed that some of the material 12 may enter the groove 34 and enhance the holding properties of the connector 10.

Each of the teeth 33 have a rear ridge surface 39. The rear ridge surfaces 39 are preferably situated generally perpendicular relative to a horizontal line with reference to FIG. 3. A perpendicular rear ridge surface tends to beneficially grasp the electrode tab, particularly when the electrode tab has a deformable layer such as the layer 12 shown in FIG. 1. At most, the ridge surfaces 39 should be inclined at an angle of between more than about 60 degrees and less than about 120 degrees relative to a horizontal line with reference to FIG. 3. If the angle is less than 60 degrees, the ridge surface 39 tends to act as a camming surface to open the jaws when an electrode 14 with a flexible layer (e.g. 12) is pulled longitudinally from the jaws of the connector, clearly an undesirable result. If the angle is more than 120 degrees, than the movable jaw 21 becomes difficult to construct as the shape becomes complicated.

Preferably, the connector 10 has electrically conductive plates or plastic inserts 41 and 42 which place the distal end portion of the fixed jaw 20 in electrical contact with the leadwire L. For example, the conductive plates 41 and 42 may be injection molded of a conductive material such as, a 40 percent (%) carbon fiber reinforced Acrylonitrile-Butadiene-Styrene material, sold under the name RTP 687 generally available from RTP Co. of Winona Minnesota (which is also a substantially X-ray translucent material). Although they are shown as two separate plates, the conductive plates 41 and 42 preferably comprise a single, monolithic conductive plate constructed from the same material. Preferably, the distal end of the fixed jaw 20 has a lip portion which helps retain the plates 41 and 42 in the fixed jaw 20. Gripping tabs 45 may be molded into fixed jaw 20 for the purpose of gripping the leadwire L.

Also preferably, the movable jaw 21 and portions of the fixed jaw 20 are constructed from a material which need not be an electrically conductive material (as long as the fixed jaw also includes conductive plastic inserts). Suitable materials includes plastics, metals and polymers. Preferably, the movable jaw 21 and portions of the fixed jaw 20 are constructed from Delrin material generally available from DuPont (which is substantially X-ray translucent). However, it should be pointed out that, optionally, the movable jaw may be constructed from an electrically conductive material such as the material used to construct conductive plastic inserts 41 and 42. Also optionally, the spring 23 may be constructed from an electrically conductive material.

Figure 7:
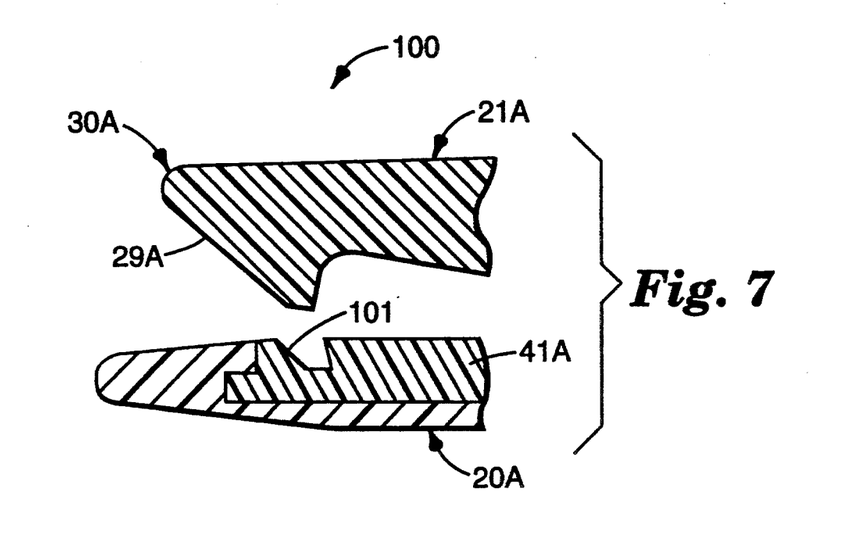
FIG. 7 is a partial cross section view of a distal end of fixed and movable jaws of a second embodiment of connector according to the present invention.
Figure 7A:
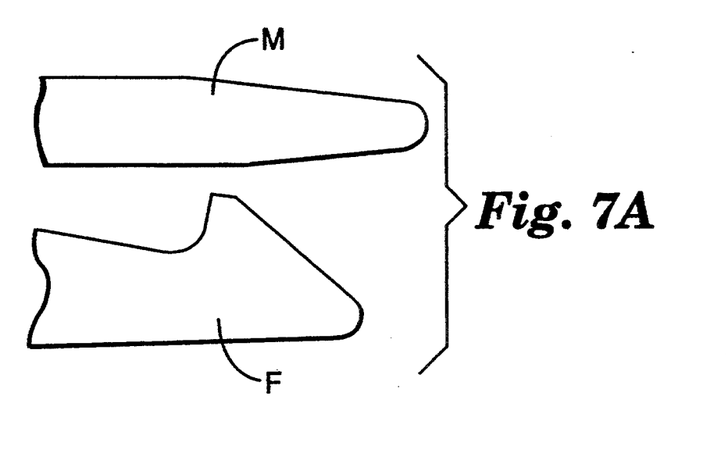
FIG. 7A illustrates a fixed jaw F with a tooth and a movable jaw M.

Referring now to FIG. 7 of the drawings, there is shown a second embodiment of connector according to the present invention generally designated by reference character 100. The connector 100 includes many features that are generally identical to the connector 10 and which have been given the same reference character to which the suffix "A" has been added.

Unlike the connector 10, in the connector 100, the fixed jaw 20A, and more particularly the conductive plate 41A has a recess 101 adapted to receive the ridge of the tooth portion. Generally speaking, the connector 100 is believed to exhibit a higher tab release force than the connector 10. However, it is believed to be more difficult to insert a tab of an electrode between the jaws 20A and 21A of the connector 100 as the tab can be caught in the recess 101 and bent.

TEST RESULTS

A connector of the type described with reference to FIGS. 2 through 6 was made as follows. The axis of the spring 23 was situated approximately 0.31 inches from the axis of the pin 19. The distance between the axis of the pin 19 and teeth 33 was approximately 0.22 inches. The total surface area of the tab engagement surfaces of the teeth was approximately 0.016 square inches. The above described connector is hereafter referred to as Connector A.

Connector B comprises an alligator type clip number M306L10 generally available from the Minnesota Mining and Manufacturing Co. (3M) of St. Paul, Minn. (or alternatively Hershman, of Germany). Connector C comprises an Alligator clip number J5 generally available from the Minnesota Mining and Manufacturing Co. (3M) of St. Paul, Minn. (or alternatively Hershman, of Germany). Connector D comprises an alligator type clip number S106L10 generally available from the Minnesota Mining and Manufacturing Co. (3M) of St. Paul, Minn. or model No. 6A2A1A21 generally available from Tronomed, Inc. of Laguna Hills, Calif. Connector E comprises a clip similar to the clip shown in U.S. Pat. No. 4,797,125 believed to have been generally available from Tronomed, Inc. of Laguna Hills, Calif. Connector F comprises a DURALINC TM clip number 2B2A-1A21 generally available from Tronomed, Inc. of Laguna Hills, Calif. Connector G comprises an Astro-Trace TM clip believed generally available from LeBlanc.

Actuation Force Measurements

Figure 8:
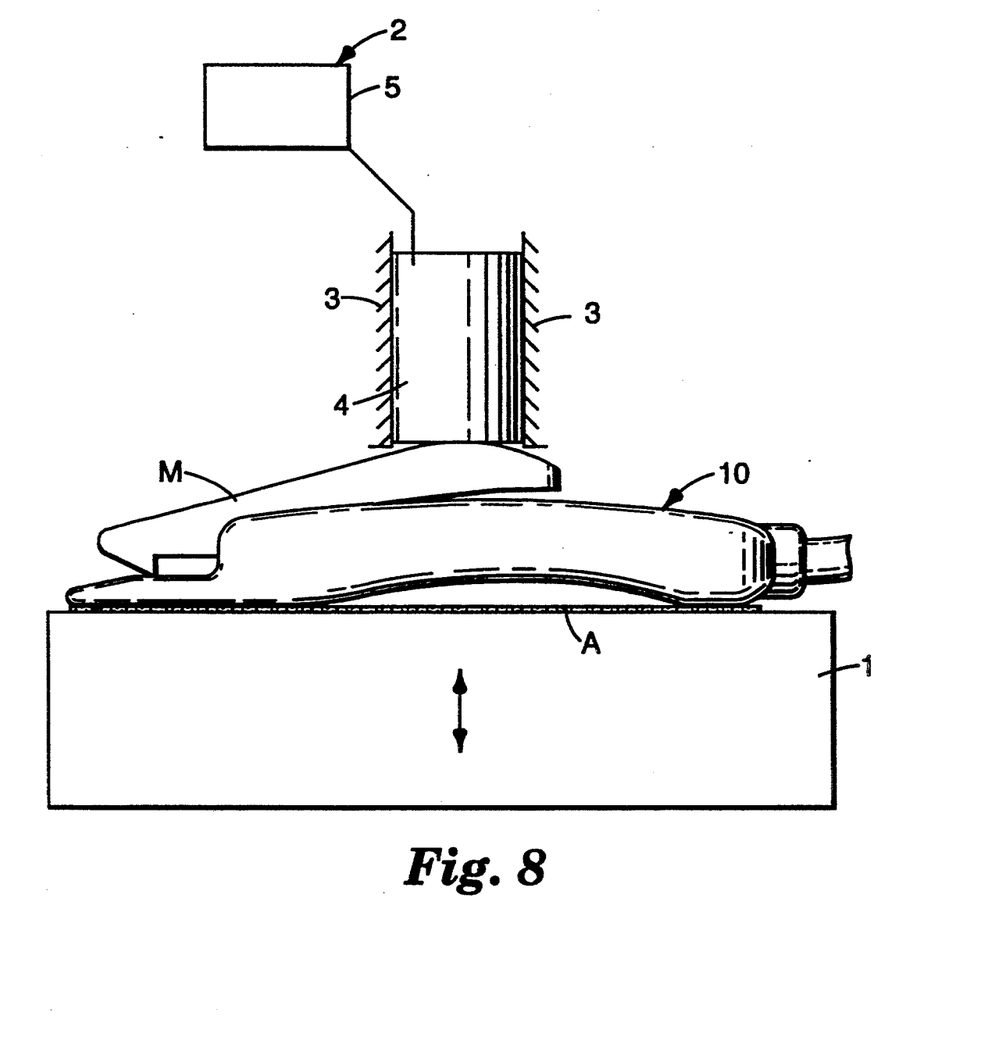
FIG. 8 is a schematic illustration of the test equipment used to conduct tab release and actuation force tests according to the present invention.

FIG. 8 is a schematic illustration of test equipment used to record actuation force measurements for the various connectors. The test equipment included a base 1, a digital force gauge 2 with jig 3, probe 4 and readout 5.

A connector to be measured was placed on the base 1 with a double sided adhesive tape A (optionally a clamp may be used) so that the movable jaw M of the connector was accessible. The movable jaw of the connector was then depressed using a digital force gauge 2, held in jig 3 allowing precision movement. In particular, the Model DFI-50 digital force gauge, commercially available from Chatillon, was used. The probe 4 of the force gauge was manually situated so that it was centered against the uppermost point of the normal finger position for opening the connector in the manner shown schematically in FIG. 8, and additional force was applied in a direction generally normal to the base 1. The force required to open the connector to its widest normal position was noted on readout 5.

The widest normal position is defined herein as the position wherein (1) the distal ends of the fixed and movable jaws are at their maximum separation due to interference of the spring itself, or (2) the distal ends of the fixed and movable jaws are at their maximum separation due to physical interference between portions of the fixed and movable jaws, or (3) the distal ends of the fixed and movable jaws are at their maximum separation due to other factors.

It is believed that ideally, the actuation force of the present invention should be at most about 9 pounds to facilitate easy opening of the jaws of the connector to its widest normal position. If the actuation force is above about 9 pounds, some users may have difficulty in using the connector, particularly those users who suffer from an ailment such as arthritis which adversely affects their ability to squeeze an object. Table 1 illustrates the results of actuation force tests run on the various connectors described above.

Tab Release Force Test

A test strip was created by providing a 3 mil (0.075 mm) thick strip of polyethylene terephthalate film 0.375 inches (0.94 cm) wide in the machine direction of the film by 2 inches (5 cm) long in the transverse direction of the film. The properties of the film included a tensile strength of 28,000 psi in the machine direction, 35,000 psi in the transverse direction, both as measured according to ASTM D882A. The coefficient of dynamic friction of this film was 0.5 as measured by ASTM D1894. The commercial source of this film was ICI Films of Wilmington, Del., branded as Melinex 505.

To this strip was laminated an adhesive tape composed of a backing of low density polyethylene film having a hardness of 48 on the Shore D scale according to ASTM 2240. The adhesive was a layer of 95.5%/4.5% isooctyl acrylate/acrylic acid copolymer adhesive, coated to a weight of 920 mg/200 cm$^2$ of backing area. The total thickness of the finished tape was 0.005 inches (0.12 mm) The commercial source of this tape was the 3M Company, of St. Paul, Minn., branded as Blenderm tape. The total thickness of the finished test strip was 0.008 inches.

A connector to be tested was used to grasp the test strip along the width axis, and was then clamped in the fixed jaw of an Instron force testing machine. The other end of the test strip was them clamped in the moving jaw of the machine, and the speed of the moving jaw was set to 30.1 cm/minute. The peak force measured before the strip was pulled free of the connector during tensile loading was measured.

It is believed that ideally, the tab release force of the present invention should be at least about 2 pounds. A tab release force of about 2 pounds is believed to be suitable for a wide variety of uses of the connector 10. If the tab release force is below about 2 pounds, then it is believed that the tab of the electrode may be easily dislodged from the connector, clearly a disadvantageous result. Table 1 illustrates the results of tab release force tests run on the various connectors described above.

TABLE 1

| Connector | Tab Release Force (Pull-off Force) (Pounds) | Actuation Force (Pounds) |
| --- | --- | --- |
| Clip A (Present Invention) | (3.9) | 3.3 |
| Clip B | (.5) | 3.0 |
| Clip C | (1.3) | 3.0 |
| Clip D | (.8) | 10.2 |
| Clip E | (1.0) | 12.5 |
| Clip F | (4.6) | 28.3 |
| Clip G | (1.0) | 11.6 |

The present invention has now been described with reference to several embodiments thereof. It will be apparent to those skilled in the art that many changes or additions can be made in the embodiments described without departing from the scope of the present invention. Thus, the scope of the present invention should not be limited to the structures described in this application, but only by structures described by the language of the claims and the equivalents of those structures.

We claim:

1. A connector for a biomedical electrode having an electrically conductive contacting tab, the connector comprising:
   a fixed jaw having a smooth, continuous, substantially planar tab engagement surface;
   a movable jaw opposite said fixed jaw, said movable jaw having a tooth portion with a tab engagement surface, and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with fixed and movable jaws spaced more closely than in the tab accept position;

biasing means for biasing the movable jaw toward the closed position; and wherein the tooth portion comprises a pair of teeth having a groove therebetween, each of said pair of teeth having a tab engagement surface.

2. A connector for a biomedical electrode having an electrically conductive contacting tab, the connector comprising:

a fixed jaw having a smooth, continuous tab engagement surface;

a movable jaw having a tooth portion with a tab engagement surface, and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with fixed and movable jaws spaced more closely than in the tab accept position;

biasing means for biasing the movable jaw toward the closed position; and wherein the fixed jaw is comprised of a substantially X-ray translucent material.

3. A connector according to claim 2 wherein the X-ray translucent material comprises a 40 percent (%) carbon fiber reinforced Acrylonitrile-Butadiene-Styrene material.

4. A connector according to claim 1 wherein the connector has an actuation force of at most about 9 pounds, and a tab release force of at least about 2 pounds.

5. A connector according to claim 4 wherein the actuation force is about 3.3 pounds, and the tab release force is about 3.9 pounds.

6. A connector according to claim 1 wherein the fixed and movable jaws have generally planar lead-in surfaces.

7. A connector according to claim 6 wherein the lead-in surfaces are situated relative to each other at an angle of about 40 degrees.

8. A connector according to claim 1 wherein the total surface area of the engagement surface of the tooth portion is about 0.016 square inches.

9. A connector according to claim 1 wherein each of said pair of teeth each have a rear ridge surface.

10. A connector according to claim 9 wherein the rear ridge surfaces are situated generally perpendicular relative to the tab engagement surface of said movable jaw.

11. A connector for a biomedical electrode having an electrically conductive contacting tab, the connector comprising:

a fixed jaw having a smooth, continuous tab engagement surface;

a movable jaw having a tooth portion with a tab engagement surface, and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with fixed and movable jaws spaced more closely than in the tab accept position;

biasing means for biasing the movable jaw toward the closed position;

wherein the movable jaw comprises proximal and distal ends, a top surface and a bottom surface, said fixed jaw comprises a bottom surface, proximal and distal end portions terminating in proximal and distal ends with the proximal end portion having a top surface, and at the proximal end of the fixed jaw, the connector is adapted to be connected to a leadwire having an outside diameter, said pivotal mounting means comprises a recess portion recessed from said top surface of the fixed jaw, and a pin situated between the proximal and distal ends of said movable jaw, and wherein, in the closed position, the distance between the top surface of the fixed jaw and the bottom surface of the movable jaw at the proximal end of the movable jaw is less than the outside diameter of the leadwire.

12. A connector according to claim 11 wherein the movable jaw comprises a cam surface generally adjacent its proximal end.

13. A connector according to claim 12 wherein the cam surface is situated at an acute angle relative to the top surface of the fixed jaw.

14. A connector according to claim 11 wherein the bottom surface of the fixed jaw comprises an arcuate portion for conforming to the shape of a user's digits.

15. A connector according to claim 11 wherein said pin is situated to allow the tab of the electrode to be situated directly between the pin and the fixed jaw.

16. A connector according to claim 1 wherein the manually engagable actuation surface comprises a locating means.

17. A connector according to claim 1 wherein said fixed and movable jaws comprise distal end portions having generally arcuate surfaces terminating in distal ends, said distal end of said movable jaw is spaced proximally from said distal end of said fixed jaw, and wherein when the connector is viewed from a top plane, distal end portion of the fixed jaw encompasses the distal end portion of the movable jaw so that a user can view when a tab is placed between the movable and fixed jaw.

18. A connector according to claim 1 wherein the connector has an overall height and an overall width, and wherein the overall width is at least 1.1 times greater than the overall height of the connector.

19. A connector according to claim 1 wherein the fixed jaw comprises a conductive plastic insert.

20. A connector for a biomedical electrode having an electrically conductive contacting tab, the connector comprising:

a fixed jaw having a smooth, continuous tab engagement surface;

a movable jaw having a tooth portion with a tab engagement surface, and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with fixed and movable jaws spaced more closely than in the tab accept position;

biasing means for biasing the movable jaw toward the closed position;

wherein the fixed jaw comprises a conductive plastic insert, and wherein the conductive plastic insert comprises:

a 40 percent (40%) carbon fiber reinforced Acrylonitrile-Butadiene-Styrene material.

21. A connector for a biomedical electrode having an electrically conductive contacting tab, the connector comprising:

a fixed jaw having a smooth, continuous tab engagement surface;

a movable jaw having a tooth portion with a tab engagement surface, and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with fixed and movable jaws spaced more closely than in the tab accept position;

biasing means for biasing the movable jaw toward the closed position; and wherein the biasing means comprises a coil spring constructed from a resilient X-ray translucent material.

22. A connector according to claim 21 wherein said resilient X-ray translucent material is a polyester elastomer.

23. A connector according to claim 17 wherein the movable jaw has a hole in the distal end portion for viewing the relative position of the tab of the electrode and the jaws of the connector.

24. A connector for a biomedical electrode having an electrically conductive contacting tab, the connector comprising:

a fixed jaw having an tab engagement surface, a movable jaw having a tab engagement surface and a manually engagable actuation surface, pivotal mounting means for mounting the movable jaw for pivotal movement relative to the fixed jaw between a tab accept position with the fixed jaw spaced from the movable jaw so that the tab of the biomedical electrode may be received between the jaws, and a closed position with the fixed and movable jaws spaced more closely than in the tab accept position, biasing means for biasing the movable jaw toward the closed position, wherein the connector has an actuation force of at most about nine (9) pounds and a tab release force of at least about two (2) pounds.

25. A connector according to claim 24 wherein one of the fixed or movable jaws comprises a tooth portion having the tab engagement surface and the other of the jaws has a smooth, continuous tab engagement surface.

26. A connector according to claim 24 wherein the fixed jaw is comprised of X-ray translucent material.

27. A connector according to claim 24 wherein the actuation force is about 3.3 pounds, and the tab release force is about 3.9 pounds.

28. A connector according to claim 24 wherein the fixed and movable jaws have generally planar lead-in surfaces.

29. A connector according to claim 28 wherein the lead-in surfaces are situated relative to each other at an angle of about 40 degrees.

30. A connector according to claim 25 wherein the tooth portion comprises a pair of teeth having a groove therebetween, each of said pair of teeth having a tab engagement surface.

31. A connector according to claim 30 wherein each of said pair of teeth each have a rear ridge surface.

32. A connector according to claim 31 wherein the rear ridge surfaces are situated generally perpendicular relative to the tab engagement surface of said movable jaw.

33. A connector according to claim 24 wherein the movable jaw comprises proximal and distal ends, a top surface and a bottom surface, said fixed jaw comprises a bottom surface, proximal and distal end portions terminating in proximal and distal ends with the proximal end portion having a top surface, and at the proximal end of the fixed jaw, the connector is adapted to be connected to a leadwire having an outside diameter, said pivotal mounting means comprises a recess portion recessed from said top surface of the fixed jaw, and a pin situated between the proximal and distal ends of said movable jaw, and wherein, in the closed position, the distance between the top surface of the fixed jaw and the bottom surface of the movable jaw at the proximal end of the movable jaw is less than the outside diameter of the leadwire.

34. A connector according to claim 33 wherein the movable jaw comprises a cam surface generally adjacent its proximal end.

35. A connector according to claim 34 wherein the cam surface is situated at an acute angle relative to the top surface of the fixed jaw.

36. A connector according to claim 33 wherein the bottom surface of the fixed jaw comprises an arcuate portion for conforming to the shape of a user's digits.

37. A connector according to claim 33 wherein said pin is situated to allow the tab of the electrode to be situated directly between the pin and the fixed jaw.

38. A connector according to claim 24 wherein the manually engagable actuation surface comprises a locating means.

39. A connector according to claim 25 wherein the tab engagement surface of said fixed jaw comprises a generally planar surface.

40. A connector according to claim 24 wherein said fixed and movable jaws comprise distal end portions having generally arcuate surfaces terminating in distal ends, said distal end of said movable jaw is spaced proximally from said distal end of said fixed jaw, and wherein when the connector is viewed from a top plane, the distal end portion of the fixed jaw encompasses the distal end portion of the movable jaw so that a user can view when a tab is placed between the movable and fixed jaw.

41. A connector according to claim 24 wherein the connector has an overall height and an overall width, and wherein the overall width is at least 1.1 times greater than the overall height of the connector.

42. A connector according to claim 24 wherein the biasing means comprises a coil spring constructed from a resilient X-ray translucent material.

43. A connector according to claim 24 wherein the movable jaw comprises a tooth portion, and the fixed jaw comprises a groove adapted to be engaged by the tooth portion of the movable jaw.

44. A connector according to claim 39 wherein the movable jaw has a hole in the distal end portion for viewing the relative position of the tab of the electrode and the jaws of the connector.

45. A connector for a biomedical electrode having an electrically conductive contacting tab, the connector comprising:
 a fixed jaw having an tab engagement surface,
 a movable jaw opposite said fixed jaw, said movable jaw having a tab engagement surface and a manually engagable actuation surface,
 pivotal mounting means for mounting the movable jaw for pivotal movement relative to the fixed jaw between a tab accept position with the fixed jaw spaced from the movable jaw so that the tab of the biomedical electrode may be received between the jaws, and a closed position with the fixed and movable jaws spaced more closely than in the tab accept position,
 biasing means for biasing the movable jaw toward the closed position,
 wherein one of the fixed or movable jaws comprises a tooth portion having the tab engagement surface and the other of the fixed or movable jaws has a smooth, continuous, substantially planar tab engagement surface; and
 wherein the tooth portion comprises a pair of teeth having a groove therebetween, each of said pair of teeth having a tab engagement surface.

46. A connector according to claim 45 wherein the fixed and movable jaws have generally planar lead-in surfaces.

47. A connector according to claim 45 wherein the fixed jaw has the tooth portion and the movable jaw has the smooth, continuous tab engagement surface.

48. A connector according to claim 45 wherein the movable jaw has the tooth portion and the fixed jaw has the smooth, continuous tab engagement surface.

49. A connector according to claim 45 wherein each of said pair of teeth each have a rear ridge surface.

50. A connector for a biomedical electrode having an electrically conductive contacting tab, the connector comprising:
 a fixed jaw having an tab engagement surface,
 a movable jaw having a tab engagement surface and a manually engagable actuation surface,
 pivotal mounting means for mounting the movable jaw for pivotal movement relative to the fixed jaw between a tab accept position with the fixed jaw spaced from the movable jaw so that the tab of the biomedical electrode may be received between the jaws, and a closed position with the fixed and movable jaws spaced more closely than in the tab accept positions.
 biasing means for biasing the movable jaw toward the closed position,
 wherein one of the fixed or movable jaws comprises a tooth portion having the tab engagement surface and the other of the fixed or movable jaws has a smooth, continuous tab engagement surface;
 wherein the movable jaw comprises proximal and distal ends, a top surface and a bottom surface,
 said fixed jaw comprises a bottom surface, proximal and distal end portions terminating in proximal and distal ends with the proximal end portion having a top surface, and at the proximal end of the fixed jaw, the connector is adapted to be connected to a leadwire having an outside diameter,
 said pivotal mounting means comprises a recess portion recessed from said top surface of the fixed jaw, and a pin situated between the proximal and distal ends of said movable jaw, and
 wherein, in the closed position, the distance between the top surface of the fixed jaw and the bottom surface of the movable jaw at the proximal end of the movable jaw is less than the outside diameter of the leadwire.

* * * * *

UNITED STATES PATENT AND TRADEMARK OFFICE
CERTIFICATE OF CORRECTION

PATENT NO.: 5,407,368
DATED: April 18, 1995
INVENTOR(S): Jerome E. Strand and Perry S. Dotterman It is certified that error appears in the above-identified patent and that said Letters Patent is hereby corrected as shown below:

Col. 16, line 22, "positions." should be --position,--.

Signed and Sealed this

Thirty-first Day of October 1995

Attest:

BRUCE LEHMAN

*Attesting Officer*     Commissioner of Patents and Trademarks